United States Patent
Kuromi et al.

(10) Patent No.: US 11,710,237 B2
(45) Date of Patent: Jul. 25, 2023

(54) IMAGE PROCESSING METHOD AND RECORDING MEDIUM

(71) Applicants: SCREEN HOLDINGS CO., LTD., Kyoto (JP); NATIONAL UNIVERSITY CORPORATION TOTTORI UNIVERSITY, Tottori (JP)

(72) Inventors: Yasushi Kuromi, Kyoto (JP); Masayoshi Kobayashi, Kyoto (JP); Tetsuya Ohbayashi, Tottori (JP); Takuya Aida, Tokyo (JP)

(73) Assignees: SCREEN Holdings Co., Ltd.; National University Corporation Tottori University

(*) Notice: Subject to any disclaimer, the term of this patent is extended or adjusted under 35 U.S.C. 154(b) by 447 days.

(21) Appl. No.: 16/966,488

(22) PCT Filed: Jan. 30, 2019

(86) PCT No.: PCT/JP2019/003106
§ 371 (c)(1),
(2) Date: Jul. 31, 2020

(87) PCT Pub. No.: WO2019/151302
PCT Pub. Date: Aug. 8, 2019

(65) Prior Publication Data
US 2021/0056704 A1 Feb. 25, 2021

(30) Foreign Application Priority Data
Jan. 31, 2018 (JP) .................. 2018-015378

(51) Int. Cl.
*G06T 7/11* (2017.01)
*G06T 7/12* (2017.01)
(Continued)

(52) U.S. Cl.
CPC ............ *G06T 7/11* (2017.01); *G01N 15/1429* (2013.01); *G06T 7/0012* (2013.01); *G06T 7/12* (2017.01);
(Continued)

(58) Field of Classification Search
CPC . G06T 7/0012; G06T 7/11; G06T 7/12; G06T 7/155; G06T 7/60; G06T 2200/04;
(Continued)

(56) References Cited

U.S. PATENT DOCUMENTS

2010/0195877 A1* 8/2010 Oonishi ................. C12M 21/06
382/128
2012/0196316 A1 8/2012 Sebesta et al. ............. 435/29
(Continued)

FOREIGN PATENT DOCUMENTS

JP 2006-338191 A 12/2006
JP 2014-016666 A 1/2014
(Continued)

OTHER PUBLICATIONS

Karnowski et al., "Optical coherence microscopy as a novel, non-invasive method for the 4D live imaging of early mammalian embryos", Scientific Reports, 2017, 7(1):4165, pp. 1-12 (Year: 2017).*

(Continued)

*Primary Examiner* — Nay A Maung
*Assistant Examiner* — Jose M Torres
(74) *Attorney, Agent, or Firm* — Ostrolenk Faber LLP

(57) ABSTRACT

A data processing method that is suitable for obtaining quantitative information from data obtained by OCT imaging. The image processing method includes acquiring original image data corresponding to a three-dimensional image of a cultured embryo obtained by optical coherence tomography imaging of the embryo and executing a region seg- (Continued)

mentation the three-dimensional image into a plurality of regions on the basis of the original image data. In the region segmentation, a local thickness calculation is performed on the three-dimensional image to determine an index value indicating a size of an object included in the three-dimensional image, the three-dimensional image is segmented into a region indicated by the index value greater than a predetermined first threshold and a region indicated by the index value less than the first threshold, and each of the regions resulting from the segmentation is further segmented by the watershed algorithm.

11 Claims, 10 Drawing Sheets

(51) Int. Cl.
  *G06T 7/155* (2017.01)
  *G01N 15/14* (2006.01)
  *G06T 7/00* (2017.01)
  *G06T 7/60* (2017.01)
  *A61B 5/00* (2006.01)

(52) U.S. Cl.
  CPC .............. *G06T 7/155* (2017.01); *G06T 7/60* (2013.01); *A61B 5/0066* (2013.01); *G06T 2200/04* (2013.01); *G06T 2207/10101* (2013.01); *G06T 2207/20152* (2013.01); *G06T 2207/30024* (2013.01); *G06T 2207/30044* (2013.01)

(58) Field of Classification Search
  CPC . G06T 2207/10101; G06T 2207/20152; G06T 2207/30024; G06T 2207/30044; G01N 15/1429; G01N 21/17; A61B 5/0066
  See application file for complete search history.

(56) References Cited

U.S. PATENT DOCUMENTS

| | | |
|---|---|---|
| 2015/0111291 A1 | 4/2015 | Aragaki |
| 2017/0140535 A1 | 5/2017 | Hamamah et al. |
| 2021/0249135 A1* | 8/2021 | Rimestad ............... G16H 50/20 |

FOREIGN PATENT DOCUMENTS

| | | |
|---|---|---|
| JP | 2015-130806 A | 7/2015 |
| JP | 2016-146132 A | 8/2016 |
| JP | 2017-521067 A | 8/2017 |

OTHER PUBLICATIONS

Extended European Search Report dated Sep. 27, 2021 for the European counterpart, European Application No. 19747001.6-1210.
Robert P. Dougherty et al.: "Computing Local Thickness of 3D Structures with ImageJ", Microscopy and Microanalysis, [Online] vol. 13, No. S02, Aug. 5, 2007, XP055810029 ISSN: 1431-9276, DOI: 10.1017/S1431927607074430 Retrieved from the Internet: URL:https://www.optinav.info/LocalThicknessEd.pdf [retrieved on Jun. 4, 2021] *the whole document*.
Karol Karnowski et al.: "Optical coherence microscopy as a novel, non-invasivemethod for the 4D live imaging of early mammalian embryos", Scientific Reports, Jun. 23, 2017, pp. 4165:1-2, XP055810445, England DOI: 10.1038/s41598-017-04220-8 Retrieved from the Internet: URL:https://www.nature.com/articles/s41598-017-04220-8.pdf [retrieved on Jun. 4, 2021] *abstract* *p. 10*.
Johannes Stegmaier et al.: "Real-Time Three-Dimensional Cell Segmentation in Large-Scale Microscopy Data of Developing Embryos", Developmental Cell, vol. 36, No. 2, 2016, pp. 225-240, XP055549589, US, ISSN: 1534-5807, DOI: 10.1016/j.devcel.2015.12.028 *abstract*.
S. Caujolle et al.: "Speckle variance OCT for depth resolved assessment of the viability of bovine embryos", Biomedical Optics Express, [Online] vol. 8, No. 11, Nov. 2017, p. 5139, XP055810497, United States, ISSN: 2156-7085, DOI: 10.1364/BOE.8.005139, Retrieved from the Internet: URL:https://www.ncbi.nlm.nih.gov/pmc/articles/PMC5695959/pdf/boe-8-11-5139.pdf retrieved on Jun. 4, 2021] *abstract* *sections 2-3*.
International Search Report dated Apr. 23, 2019 in corresponding PCT International Application No. PCT/JP2019/003106.
Written Opinion dated Apr. 23, 2019 in corresponding PCT International Application No. PCT/JP2019/003106.

* cited by examiner

IMAGE PROCESSING METHOD AND RECORDING MEDIUM

CROSS-REFERENCE TO RELATED APPLICATIONS

The present application is a 35 U.S.C. §§ 371 national phase conversion of International Application No. PCT/JP2019/003106, filed Jan. 30, 2019, which claims priority to Japanese Patent Application No. 2018-015378, filed Jan. 31, 2018, the contents of both of which are incorporated herein by reference. The PCT International Application was published in the Japanese language.

TECHNICAL FIELD

The present invention relates to an image processing technique for providing useful information to a user to assess an embryo using data corresponding to a three-dimensional image of the embryo obtained by tomographic imaging.

BACKGROUND ART

In assisted reproductive technologies intended for fertility treatment, for example, after an embryo resulting from external fertilization (fertilized egg) is cultured for a certain period of time, the embryo is returned into a womb. However, This does not always result in a high success rate while imposing heavy psychological and economical burdens on a patient. To solve this problem, effort has been made to find a method of correctly judging the condition of an embryo to be cultured.

An assessment of whether embryo culture proceeds favorably has conventionally been made, generally by a doctor or a clinical embryologist through visual inspection using a microscope, for example. As indexes to this judgment, Veeck classification or Gardner classification has widely been used, for example. However, these classifications merely provide rough judgment criteria for morphological features of an embryo. Under present circumstances, a final assessment is made depending on a subjective judgment by a person to make the assessment. Hence, a technique for allowing making of an objective and quantitative judgment has been desired.

As an example, patent literature 1 suggests a technique of assessing the quality of an embryo by applying non-invasive tomographic imaging technology such as optical coherence tomography (OCT). According to this technique, a three-dimensional image of the embryo is reconstructed from a tomographic image obtained by OCT imaging. Then, on the basis of the reconstructed three-dimensional image, the quality of the embryo is assessed using criteria that are morphological criteria for the embryo such as the number of blastomeres, blastomere regularity, and a fragmentation rate.

CITATION LIST

Patent Literature

[PTL 1] JP2017-521067

SUMMARY

Technical Problem

The foregoing literature states that assessment of an embryo is feasible on the basis of a three-dimensional image obtained by OCT imaging. Also, this literature discloses examples of three-dimensional images of the embryo viewed from various directions. However, this literature does not state a particular way of processing an image or calculation of a quantitative index. Namely, this conventional technique was made by merely replacing a two-dimensional image such as a microscope image having been used for visual observation so far with a three-dimensional image. Hence, while this technique can be used for assisting in assessment of an embryo more effectively than in a conventional case of using a two-dimensional image, it cannot be considered to provide sufficiently effective use of information obtained from a result of OCT imaging.

Under Veeck classification or Gardner classification described above, for example, an embryo is judged to be of good quality on condition that there is favorable uniformity of the sizes or shapes of cells in the embryo. For this judgment, a user will find it convenient if a quantitative index for assessment of the size or shape of each cell individually forming the embryo can be obtained from imaging data. In this regard, the foregoing conventional technique provides an exemplary way of display in which a pellucid zone on the surface of an embryo is erased to expose inner cells or an exemplary way of display in which the embryo is rotated to allow observation of the embryo from various directions (FIGS. 5A to 5I, for example). However, this does not contribute to the quantification for assessment described above.

As described above, a tomographic image obtained by OCT imaging and a three-dimensional image constructed from the tomographic image have the potential to provide much useful information for assessment of an embryo in terms of the internal configuration of the embryo, for example. However, a specific data processing method responsive to this issue has yet to be established so far.

Solution to Problem

The present invention has been made in view of the foregoing problem, and is intended to assist in assessment of an embryo by a user effectively by providing a data processing method suitable for obtaining quantitative information from data obtained by OCT imaging.

To achieve the foregoing intention, one aspect of the present invention is directed to an image processing method comprising: acquiring original image data corresponding to a three-dimensional image of a cultured embryo obtained by optical coherence tomography imaging of the embryo; and segmenting the three-dimensional image into a plurality of regions on the basis of the original image data. In the region segmentation step, the local thickness calculation is performed on the three-dimensional image to determine an index value indicating the size of an object included in the three-dimensional image, the three-dimensional image is segmented into a region indicated by the index value greater than a predetermined first threshold and a region indicated by the index value less than the first threshold, and each of the regions resulting from the segmentation is segmented by the watershed algorithm.

Another aspect of the present invention is directed to a program for causing a computer to perform each of the foregoing process. Another aspect of the present invention is directed to a computer-readable storage medium storing the program.

As will be described in detail later, an embryo, particularly, a fertilized egg of a mammal has a practically spherical outer shape. The internal configuration thereof is an aggregate of a plurality of cells that are also practically spherical or ellipsoidal. To assess each cell individually forming such an embryo, a way in which a spatial region is occupied by each cell is required to be determined, namely, a boundary between cells in three-dimensional space is required to be defined.

For definition of such a boundary, region segmentation process of a three-dimensional image such as an OCT image is applicable. For example, the watershed algorithm as a publicly-known image processing algorithm is applicable. However, knowledge of the inventors of the present application shows that, in many cases, a result of region segmentation by the watershed algorithm diverges from a boundary between cells determined from a three-dimensional image by a skilled person. Erroneous segmentation is considered to be caused by reasons such as the unclearness of a boundary between cells in a three-dimensional image of an embryo to become more serious gradually in response to increase in the number of cells formed by cleavage, inclusion of a polar body, a micro structure (fragment, for example) caused by imperfect cell division, or image noise, etc. in this three-dimensional image, and others.

In this regard, according to the present invention, to clarify a boundary between cells or a boundary between a cell and a relatively small structure other than cells, an image processing technique called the local thickness calculation is used (for application to a three-dimensional image, this technique is particularly called 3D local thickness calculation). According to the 3D local thickness calculation, an object is expressed in terms of a gradation on the basis of the magnitude of the radius of a sphere inscribed in an object in a three-dimensional image. For example, an object having a relatively large configuration is expressed by high gradation. By contrast, a relatively small object is expressed by lower gradation. Using such a value (in this case, a gradation value) depending on the size of an object as an index value makes it possible to distinguish between a relatively large object corresponding to a cell, for example, and a tiny object corresponding to a fragment, for example. Additionally, a boundary between cells is given clearly. Thus, by performing region segmentation by the watershed algorithm further on a region resulting from the foregoing segmentation, a segmentation result thereby obtained can be given a higher degree of agreement with an actual boundary between cells, for example.

As described above, by assessing a relatively large one of the regions resulting from the segmentation according to the foregoing image processing method individually as each cell, it becomes possible to obtain various types of index values indicating the shape, size, and others of the cell quantitatively. For example, whether an index value obtained by the local thickness calculation is greater or less than the predetermined first threshold can be used for distinguishing between a region corresponding to a cell and other regions.

Another aspect of the present invention is directed to an image processing method of segmenting a three-dimensional image of an embryo into a plurality of regions by the foregoing image processing method, and judging the first region of the plurality of regions indicated by the index value greater than the first threshold to be a blastomere aggregate. This makes it possible to distinguish between a cell as a relatively large structure in an embryo and a relatively small structure in the embryo such as a polar body or a fragment. Further, a feature such as a three-dimensional shape of each structure is obtained quantitatively to be available for use in assessment of the embryo.

Advantageous Effects of Invention

As described above, the present invention allows acquisition of quantitative information required for assessment of each cell forming a cultured embryo from data obtained by OCT imaging of the embryo.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DESCRIPTION OF EMBODIMENTS

A specific embodiment of an image processing method according to the present invention will be described below. This embodiment is the realization of the image processing method according to the present invention. In this embodiment, an embryo cultured in a culture medium (culture solution) carried in a culture container is tomographically imaged by optical coherence tomography (OCT) technology. On the basis of data obtained by the imaging, quantitative information about cells forming the embryo is output. This embodiment is intended to assist in assessment of the embryo by a user (more specifically, by a doctor or a clinical embryologist). For example, the image processing method of this embodiment is applicable to culture of a fertilized egg for assisted reproductive technologies with the intention of acquiring knowledge for judging whether the culture proceeds favorably.

The configuration of an image processing apparatus for imaging of obtaining a tomographic image and the principles of the imaging by the image processing apparatus will be described first. Image processing using data acquired by the imaging will be described next.

Figure 1:
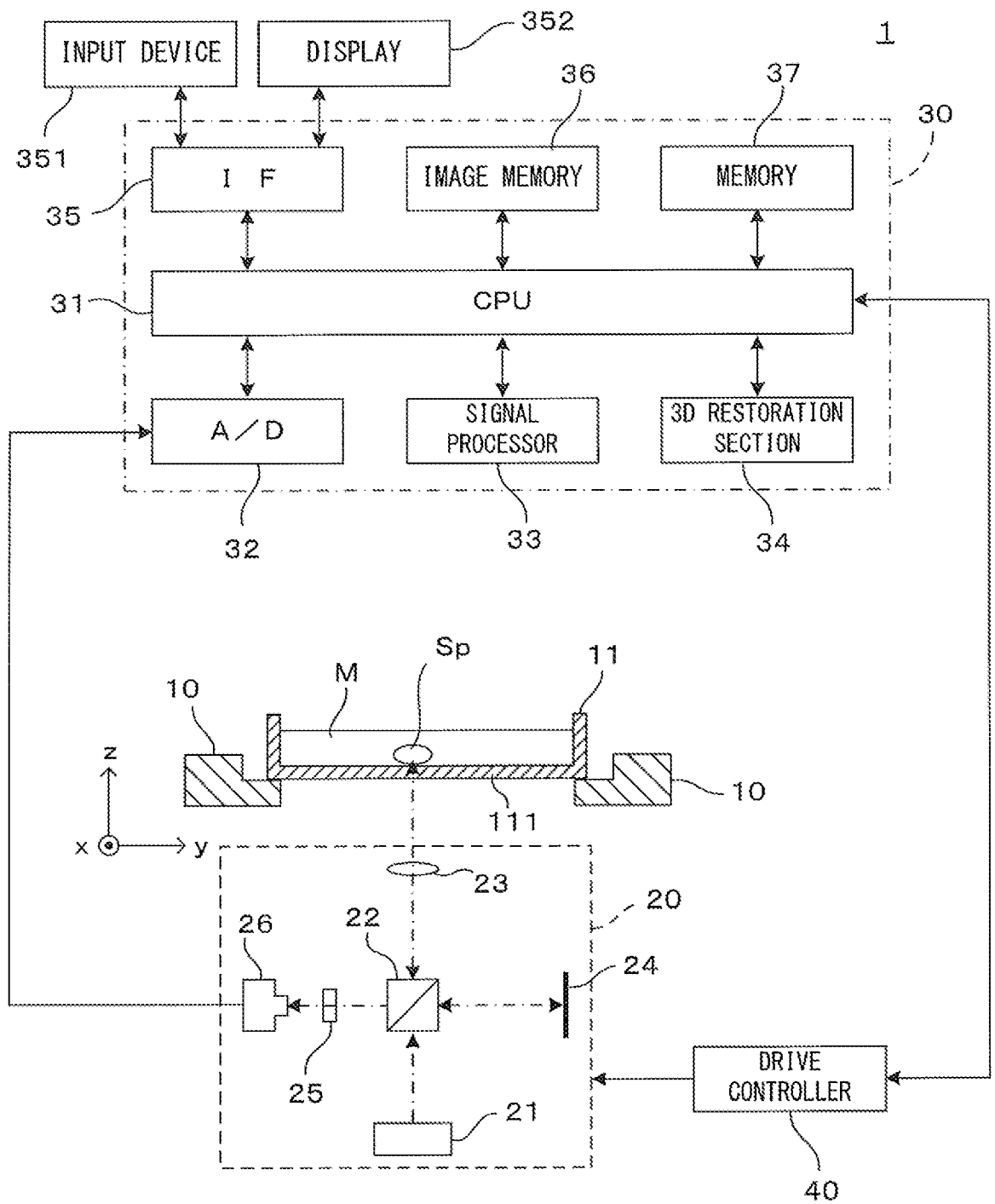
FIG. 1 is a drawing showing a constructional example of an image processing apparatus for tomographic imaging.

FIG. 1 is a drawing showing a constructional example of an image processing apparatus for tomographic imaging. The image processing apparatus 1 tomographically images an embryo cultured in a culture medium as an imaging object, processes the obtained tomographic image and generates a three-dimensional (3D) image of the imaging object. For unified presentation of the directions in drawings, the XYZ orthogonal coordinate axes are established as shown in FIG. 1. The XY plane is a horizontal surface. The Z axis represents the vertical axis, in more detail, the (−Z) direction represents the vertically downward direction.

The image processing apparatus 1 comprises a holder 10. The holder 10 holds a culture container 11 in an approximately horizontal posture in such a manner that its opening is directed toward above. The culture container (hereinafter, simply referred to as "container") 11 is called a "dish" or a "plate" having a flat bottom surface made of transparent and uniform glass or resin. A predetermined amount of an appropriate culture medium M is poured in the container 11 in advance, and a sample Sp (an embryo in this embodiment) is cultured in the medium at the bottom part 111 of the container 11. Although FIG. 1 shows only one sample Sp, a plurality of samples Sp may be cultured in one container 11.

An imaging unit 20 is disposed below the container 11 which is held by the holder 10. An optical coherence tomography (OCT) apparatus capable of imaging tomographic images of an imaging object in a non-contact and non-destructive (non-invasive) manner is used as the imaging unit 20. As described in detail later, the imaging unit 20 which is an OCT apparatus comprises a light source 21 which emits illumination light for an imaging object, a beam splitter 22, an objective optical system 23, a reference mirror 24, a spectroscope 25 and a photo-detector 26.

Further, the image processing apparatus 1 comprises a control unit 30 which controls operations of the apparatus and a drive controller 40 which controls movement of movable parts of the imaging unit 20. The control unit 30 comprises a CPU (Central Processing Unit) 31, an A/D convertor 32, a signal processor 33, a 3D restoration section 34, an interface (IF) section 35, an image memory 36 and a memory 37.

The CPU 31 governs operations of the entire apparatus by executing a predetermined control program. The control program executed by the CPU 31 and data which are generated during processing are saved in the memory 37. The A/D convertor 32 converts a signal which the photo-detector 26 of the imaging unit 20 outputs in accordance with the amount of received light into digital image data. The signal processor 33 performs image processing described later based upon a digital data outputted from the A/D converter 32, thereby generates a tomographic image of the imaging object. Based upon image data of a plurality of tomographic images, the 3D restoration section 34 generates a three-dimensional image (3D image) of the imaged embryo. The image memory 36 saves the image data of the tomographic images generated by the signal processor 33 and the image data of the stereoscopic image generated by the 3D restoration section 34. The signal processor 33 and the 3D restoration section 34 may be configured as dedicated hardware. Further, these may be realized as software by a program executed by the CPU 31.

The interface section 35 realizes communication between the image processing apparatus 1 and outside. More specifically, the interface section 35 has a function of communicating with external equipment, and a user interface function of accepting manipulation by a user and informing the user of various types of information. For this purpose, an input device 351 and a display section 352 are connected to the interface section 35. The input device 351 is for instance a key board, a mouse, a touch panel or the like which can accept manipulation and entry concerning selection of the functions of the apparatus, setting of operating conditions, etc. The display section 352 comprises a liquid crystal display for example which shows various types of processing results such as the tomographic images imaged by the imaging unit 20 and the three-dimensional image generated by the 3D restoration section 34.

Further, the CPU 31 sends a control command to the drive controller 40. The drive controller 40 makes the movable parts of the imaging unit 20 execute predetermined operation in accordance with the control command. As described next, the tomographic images of the sample (specifically, the embryo) which are the imaging object are obtained owing to combination of scan moving of the imaging unit 20 executed by the drive controller 40 and detection of the amount of the received light by the photo-detector 26.

Figure 2A:
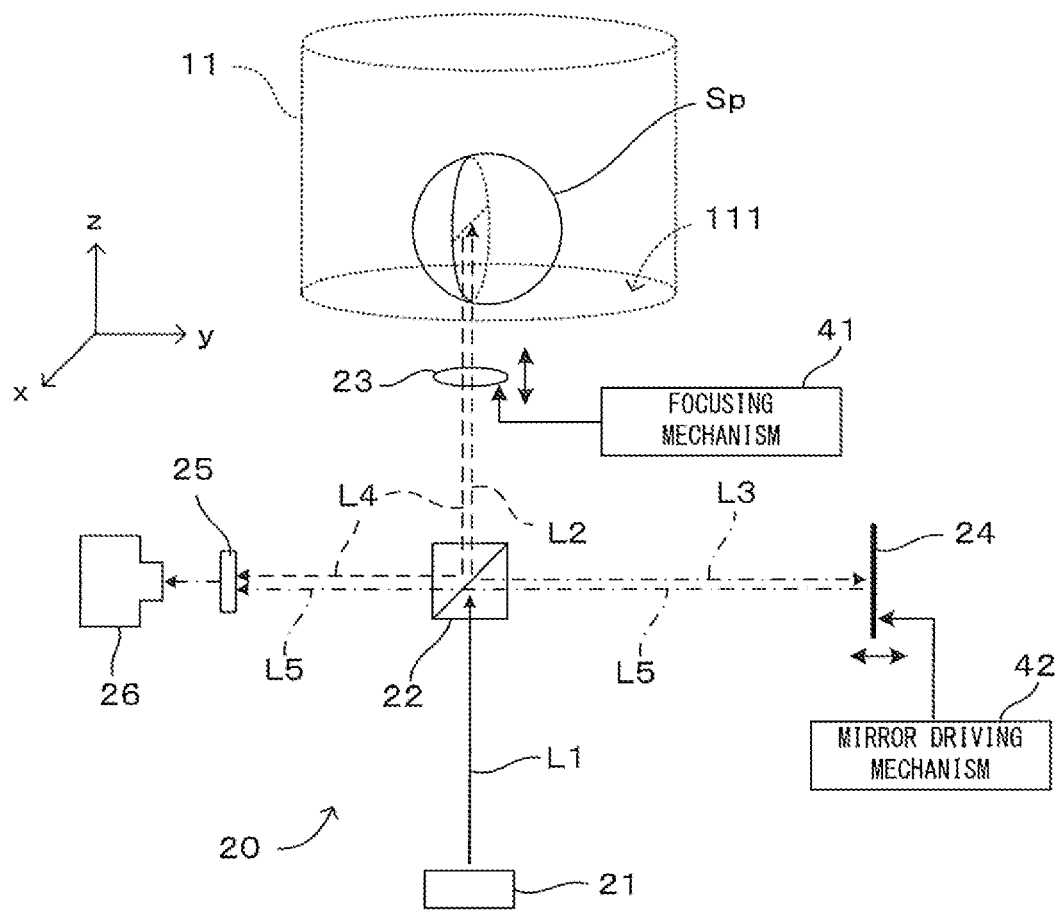
FIG. 2A is a first drawing for describing the principle of imaging in this image processing apparatus.
Figure 2B:
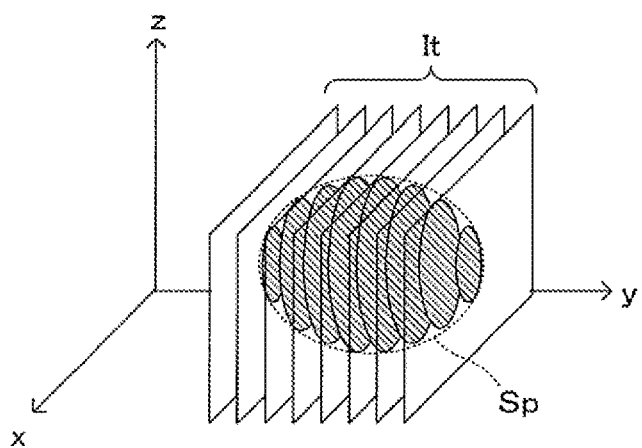
FIG. 2B is a second drawing for describing the principle of imaging in this image processing apparatus.

FIGS. 2A and 2B are drawings for describing the principle of imaging in this image processing apparatus. More specifically, FIG. 2A is a drawing which shows optical paths inside the imaging unit 20, and FIG. 2B is a schematic drawing which shows tomographic imaging of a sample. As described earlier, the imaging unit 20 works as an optical coherence tomography (OCT) apparatus. Although the sample Sp is drawn approximately as a sphere for an illustration, a shape of the sample in practical imaging is not limited to this.

In the imaging unit 20, from the light source 21 which includes a light emitting element such as a light emitting diode or a super luminescent diode (SLD) for instance, a low-coherence light beam L1 containing a wide-range wavelength components is emitted. The light beam L1 impinges upon the beam splitter 22 and diverges. Some light L2 indicated by the broken-line arrow propagates toward the container 11, and some light L3 indicated by the arrow of long dashed short dashed line propagates toward the reference mirror 24.

The light L2 propagating toward the container 11 is incident on the container 11 by way of the objective optical system 23. More specifically, the light L2 emitted from the beam splitter 22 is incident on the bottom part 111 of the container 11 via the objective optical system 23. The objective optical system 23 has a function of converging the light L2 propagating from the beam splitter 22 toward the container 11 to the sample Sp in the container 11 and a function of collecting the reflected light emitted from the sample Sp and causing it to propagate toward the beam splitter 22. Although the objective optical system 23 is illustrated as a single objective lens in FIG. 2A, the objective optical system 23 may include a plurality of optical elements.

The objective optical system 23 is movable in the Z direction by a focusing mechanism 41 which is disposed to the drive controller 40. This enables the focus position of the objective optical system 23 with respect to the imaging object to be changed in the Z direction. An optical axis of the objective optical system 23 is parallel to a vertical direction and, therefore, perpendicular to the bottom part 111 of the container 11 in the form of a flat plate. Further, an incident direction of illumination light on the objective optical system 23 is parallel to the optical axis. The arrangement of the objective optical system 23 is determined such that a light center of the light coincides with the optical axis.

The incident light L2 via the bottom part 111 is reflected at the surface of the sample Sp unless the sample Sp transmits the light beam L2. On the other hand, when the sample Sp has a property of transmitting the light beam L2 to a certain extent, the light beam L2 propagates into inside the sample Sp and is reflected by a structure element which is inside the sample. When the near infrared rays for instance are used as the light beam L2, it is possible to allow the incident light to reach even inside the sample Sp. The reflected light from the sample Sp is irradiated as scattered light in various directions. Out of that, light L4 irradiated within a light collection range of the objective optical system 23 is collected by the objective optical system 23 and sent to the beam splitter 22.

The reference mirror 24 is supported in such a manner that a reflection surface thereof is perpendicular to an incident direction of the light L3. The reference mirror 24 is movable in a direction (Y direction in FIG. 2A) along the incident direction of the light L3 by a mirror driving mechanism 42 provided in the drive controller 40. The light L3 incident on the reference mirror 24 is reflected by the reflection surface and propagates toward the beam splitter 22 as light L5 propagating in an opposite direction along an incident optical path. This light L5 becomes reference light. By changing the position of the reference mirror 24 by the mirror driving mechanism 42, an optical path length of the reference light changes.

The reflected light L4 reflected by a surface or an internal reflecting surface of the sample Sp and reference light L5 reflected by the reference mirror 24 are incident on the photo-detector 26 via the beam splitter 22. At this time, interference due to a phase difference between the reflected light L4 and the reference light L5 occurs, but an optical spectrum of interference light differs depending on a depth of the reflecting surface. That is, the optical spectrum of the interference light has information on a depth direction of the imaging object. Thus, a reflected light intensity distribution in the depth direction of the imaging object can be obtained by spectrally diffracting the interference light at each wavelength to detect a light quantity and Fourier transforming a detected interference signal. An OCT imaging technique based on such a principle is called Fourier domain OCT (FD-OCT).

The imaging unit 20 of this embodiment is provided with a spectroscope 25 on an optical path of the interference light from the beam splitter 22 to the photo-detector 26. A spectroscope utilizing a prism, a spectroscope utilizing a diffraction grating and the like can be, for example, used as the spectroscope 25. The interference light is spectrally diffracted for each wavelength component and received by the photo-detector 26.

By Fourier-transforming the interference signal output from the photo-detector 26 according to the interference light detected by the photo-detector 26, the reflected light intensity distribution of the sample Sp in the depth direction, i.e. in the Z direction at the incident position of the light beam L2 is obtained. By scanning the light beam L2 incident on the container 11 in the X direction, the reflected light intensity distribution in a plane parallel to an XZ plane is obtained, with the result that a tomographic image of the sample Sp having this plane as a cross-section can be generated. In this specification, a series of operations for obtaining one tomographic image It in a cross-section parallel to the XZ plane by beam scanning in the X direction is referred to as one imaging.

Images are obtained by changing the incident position of the light L2 along the Y direction over multiple steps and imaging a tomographic image for every change. As shown in FIG. 2B, a number of tomographic images It of the sample Sp are obtained along cross-sectional surfaces which are parallel to the XZ plane. As the scan pitch in the Y direction is reduced, it is possible to obtain image data with sufficient resolution to grasp the stereoscopic structure of the sample Sp. Scan movements of the light beam in X and Y direction are realized as an optical device (not shown) changing an optical path such as a Galvanometer mirror changes the incident position of the light beam to X and Y direction. Further, a process in which the container 11 carrying the sample Sp and imaging unit 20 relatively move to X and Y direction is also applicable.

Note that, in the imaging unit 20 of the above description, it is the beam splitter 22 that has a function of dividing the light from the light source 21 to the illumination light and the reference light and a function of mixing the signal light and the reference light to cause interference. On the other hand, some of OCT image processing apparatuses are known to have a dividing/mixing function, for example, an optical fiber coupler as described below.

Figure 3A:
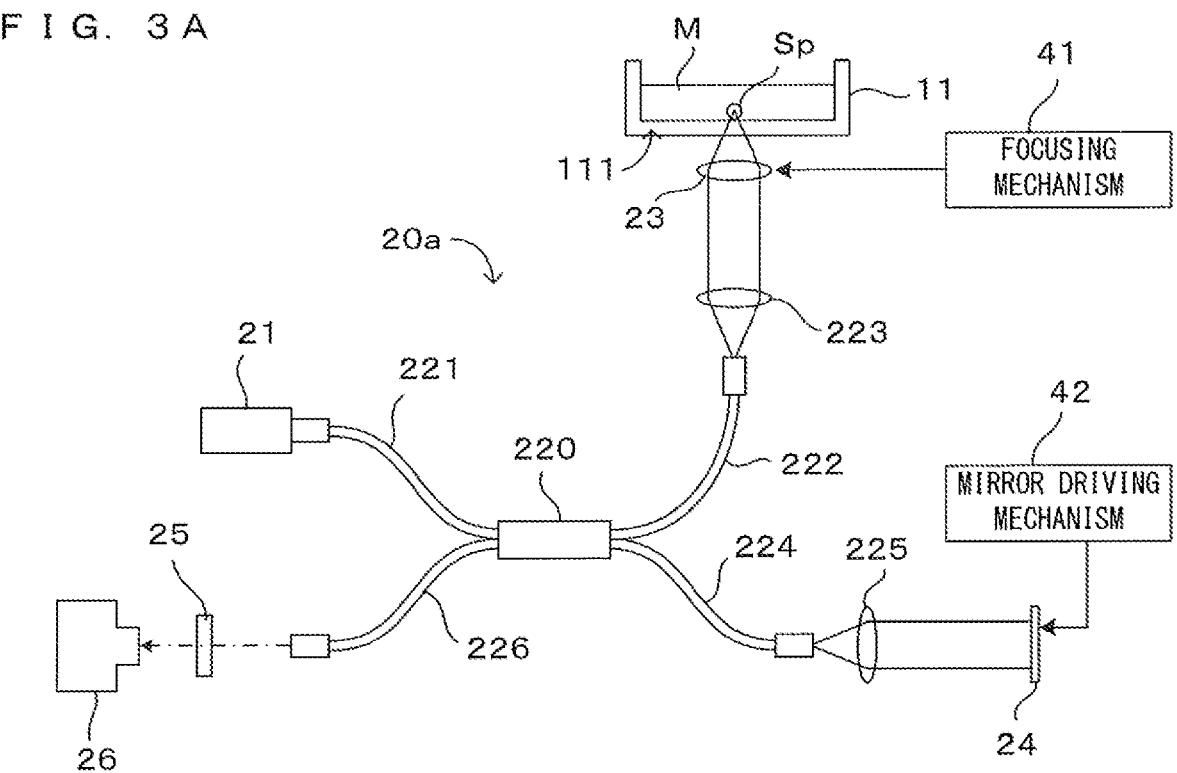
FIG. 3A is a first diagram showing other configuration examples of the OCT apparatus.
Figure 3B:
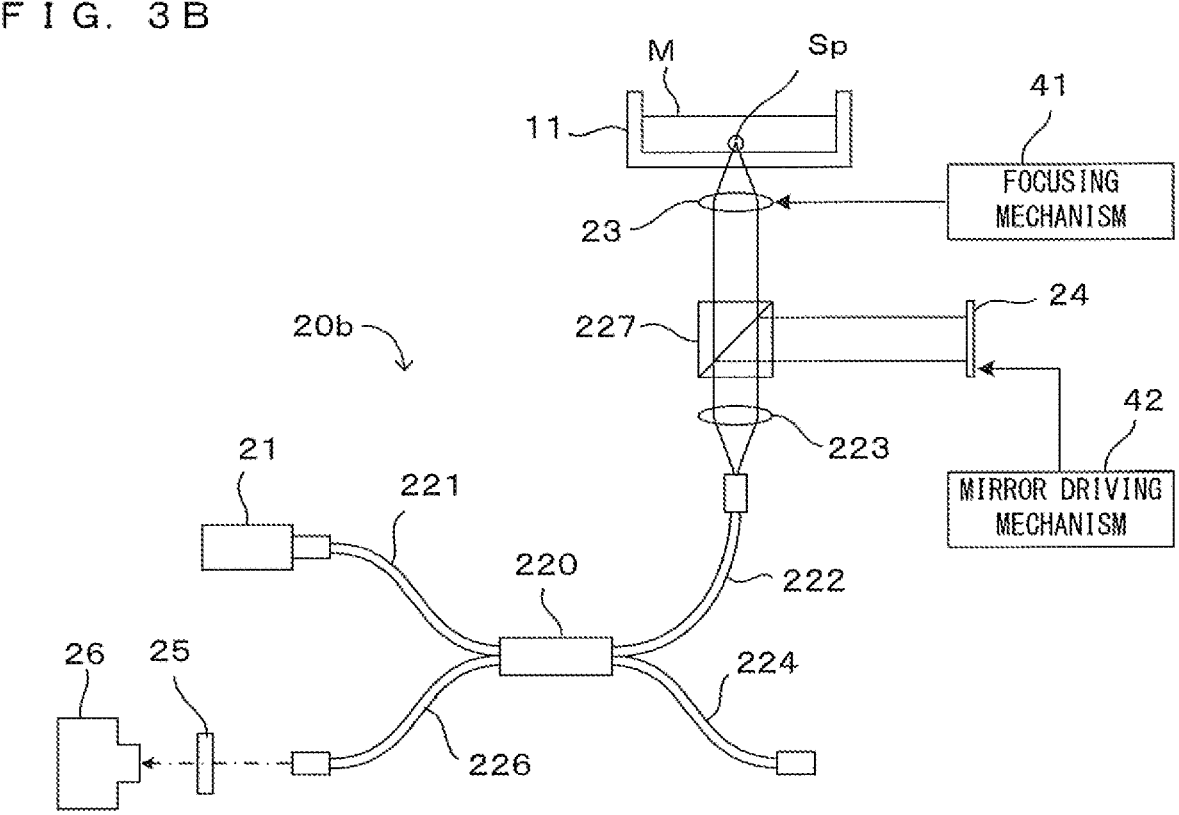
FIG. 3B is a second diagram showing other configuration examples of the OCT apparatus.

FIGS. 3A and 3B are diagrams showing other configuration examples of the OCT apparatus. Note that, in the following description, constituent components same as or corresponding to those of other embodiments are denoted by the same reference signs to facilitate understanding. The structures and functions thereof are basically the same as those of the embodiment unless particularly described, and thereby the detail description is omitted. An OCT imaging principle for detecting interference light by the optical fiber coupler is not described in detail since it is same as the above embodiment.

In an example shown in FIG. 3A, an imaging unit 20a includes an optical fiber coupler 220 instead of the beam splitter 22 as a dividing/mixing optical device. One 221 of optical fibers constituting the optical fiber coupler 220 is connected to a light source 21 and low-coherence light emitted from the light source 21 is branched into lights to two optical fibers 222, 224 by the optical fiber coupler 220.

The optical fiber 222 constitutes an object side optical path. More specifically, light emitted from an end part of the optical fiber 222 is incident on an objective optical system 23 via a collimator lens 223. Reflected light (signal light) from an imaging object is incident on the optical fiber 222 via the objective optical system 23 and the collimator lens 223.

Another optical fiber 224 constitutes a reference side optical path. More specifically, light emitted from an end part of the optical fiber 224 is incident on a reference mirror 24 via a collimator lens 225. Reflected light (reference light) from the reference mirror 24 is incident on the optical fiber 224 via the collimator lens 225. The signal light propagating in the optical fiber 222 and the reference light propagating in the optical fiber 224 interfere in the optical fiber coupler 220. The interference light is incident on a photo-detector 26 via an optical fiber 226 and a spectroscope 25. An intensity distribution of the reflected light on the imaging object is obtained from the interference light received from the photo-detector 26 as in the above principle.

Also in an example shown in FIG. 3B, an optical fiber coupler 220 is provided in an imaging unit 20b. However, an optical fiber 224 is not used and a collimator lens 223 and a beam splitter 227 as an optical device are provided on an optical path of light emitted from an optical fiber 222. As the principle described above, an objective optical system 23 and a reference mirror 24 are arranged on two optical paths branched by the beam splitter 227. In such a configuration, signal light and reference light are mixed by the beam splitter 227. Interference light generated thereby is guided to a photo-detector 26 through the optical fibers 222, 226.

In these examples, the optical path of each light propagating in a space is partially replaced by an optical fiber in the principle diagram of FIG. 2A, but the operation principle is the same. Also in these examples, the focusing mechanism 41 moves the objective optical system 23 in directions toward and away from the container 11, whereby a focal depth of an objective optical system 23 with respect to the imaging object can be adjusted. Further, the mirror driving mechanism 42 moves the reference mirror 24 along the incident direction of the light, whereby the optical path length of the reference light can be changed.

An imaging operation by this image processing apparatus 1 is described below. The same imaging operation can be performed regardless of the configuration of the imaging unit using the beam splitter described above or that using an optical fiber coupler. Further, an imaging apparatus for tomographic imaging is not limited to the above mentioned FD-OCT imaging apparatus. For example, an image processing apparatus such as a time-domain OCT (TD-OCT) based on different imaging principles is also applicable. In the image processing method described below, reflected light of illumination light incident on each position in three-dimensional space including the sample Sp and its surrounding is used as signal light. Data containing association between a position in the three-dimensional space and signal intensity corresponding to the quantity of the signal light from this position is used for the processing. Thus, any imaging method available for use for acquiring such data is applicable.

FIGS. 4A through 4D are schematic views illustrating representative configurations of embryos to be processed. When the image processing apparatus 1 is used for fertility treatment, for example, a fertilized egg resulting from external fertilization and in an initial stage of culture is an imaging object by the image processing apparatus 1. As is already known, after an egg is fertilized, cleavage starts. After a state called a morula is passed, a blastocyst is formed. The image processing method of this embodiment is to provide a user with information suitable for observation of an embryo in a period from a moment immediately after fertilization to a blastocyst stage, for example.

Figure 4A:
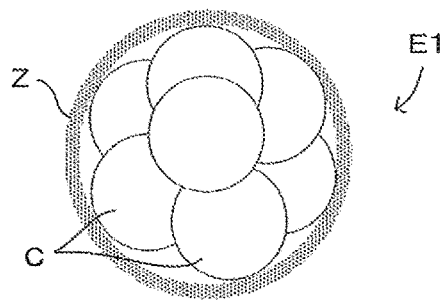
FIG. 4A is a first schematic view illustrating representative configurations of embryos to be processed.
Figure 4B:
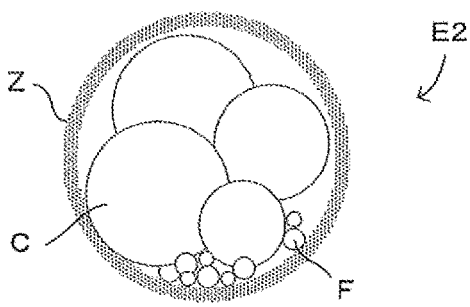
FIG. 4B is a second schematic view illustrating representative configurations of embryos to be processed.

FIG. 4A schematically shows the configuration of an embryo in an initial stage (in a period from a four-cell stage to a morula stage, for example). An embryo E1 has a practically spherical outer shape. The surface of the embryo E1 is covered by a jelly glycoprotein layer Z called a pellucid zone. A plurality of cells C formed by cell division of a fertilized egg is included inside the embryo E1. As shown in FIG. 4A, if culture proceeds favorably, the interior of the pellucid zone Z is occupied by the cells C of uniform size. As cleavage proceeds further, the number of the cells increases. Veeck classification defines that there is desirably uniformity between these cells. By contrast, if the culture does not proceed in a favorable condition, non-uniformity may be caused between the sizes of the cells C or tiny pieces called fragments may be caused in addition to the cells C formed by the cleavage, like in an embryo E2 shown in FIG. 4B. While FIG. 4B shows the occurrences of both the non-uniformity of the sizes of the cells C and fragments F, only one of these may occur.

In either case, this condition of the embryo is determined to be inferior to that shown in FIG. 4A. Thus, regarding an initial embryo up to a morula stage, indexes for assessment of a culture condition may be whether the sizes of the cells C formed by cleavage are uniform, whether the surface of each cell C is smooth, whether the fragment F has occurred, and others.

Figure 4C:
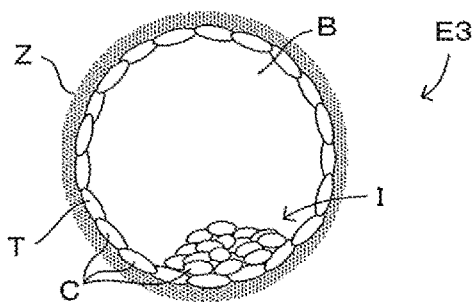
FIG. 4C is a third schematic view illustrating representative configurations of embryos to be processed.
Figure 4D:
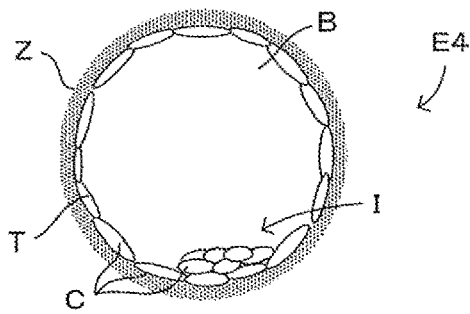
FIG. 4D is a fourth schematic view illustrating representative configurations of embryos to be processed.

FIGS. 4C and 4D schematically show internal configurations of embryos in a blastocyst stage. FIG. 4C shows an embryo E3 in a favorable condition. FIG. 4D shows an embryo E4 in a condition inferior to that of FIG. 4C. As shown in FIG. 4C, in a blastocyst stage, the cells resulting from the development of cleavage are aligned in a thin layer along the surface of the embryo to form a trophectoderm T. A cavity called a blastocoel B is generated in internal space surrounded by the trophectoderm T. An inner cell mass I with a large number of the dense cells C is formed in a part of the internal space.

In the embryo E3 in a good condition, the trophectoderm T is formed of a large number of the dense cells C, and the inner cell mass I is also formed of a relatively large number of the cells C. By contrast, in the embryo E4 in a condition inferior to that of the embryo E3, the trophectoderm T may be formed of a smaller number of the sparse cells C, or the inner cell mass I may be formed of a small number of cells to be reduced in size, for example. Thus, a culture condition of an embryo can be judged using an index including the thickness or density of the trophectoderm T, and the size and density of the inner cell mass I.

Figure 5:
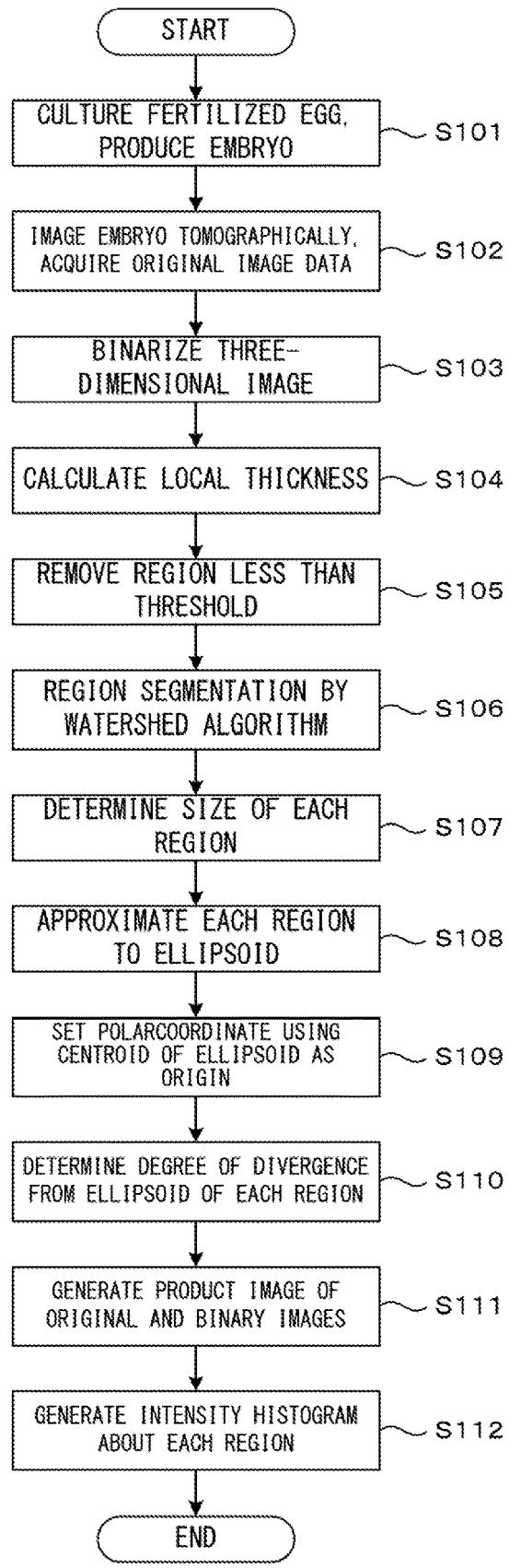
FIG. 5 is a flowchart showing the image processing method of this embodiment.

FIG. 5 is a flowchart showing the image processing method of this embodiment. Step S101, which is part of a series of processes described below, is performed in an appropriate incubator prepared separately from the image processing apparatus 1. Processes from step S102 and its subsequent steps are realized by causing the CPU 31 in the image processing apparatus 1 to execute the control program stored in advance in the memory 37. However, this is not the only way of implementing these processes.

For example, step S103 and its subsequent steps in FIG. 5 can be performed by a computer device having a general calculation function and a general image output function. In some configurations, the computer device different from the image processing apparatus 1 may receive OCT imaging data from the image processing device 1 and perform these processes. This allows the CPU 31 in the image processing device 1 to perform only the process specialized for imaging. In this way, processing load on the CPU 31 is reduced.

The details of the specific processes will be described below. First, an embryo to be assessed is cultured in an appropriate culture environment (step S101). The image processing apparatus 1 images the cultured embryo by OCT imaging at appropriate timing (step S102). Data obtained by the imaging, more specifically, data indicating the intensity of reflected light from each position in three-dimensional space including the embryo and its surrounding is stored as original signal data into the memory 37 or the image memory 36. This original signal data is used to generate pixel data (voxel data) about each coordinate position in the three-dimensional space, thereby allowing formation of a three-dimensional image of the embryo such as that shown in patent literature 1 and output of the same as an image. The generated voxel data is stored as original image data into the image memory 36.

For subsequent processes, the three-dimensional image is binarized (step S103). For example, of pixels expressed by the voxel data, a pixel having a pixel value (brightness value) exceeding a prescribed threshold is expressed by "1" and a pixel having a pixel value less than the threshold is expressed by "0." In this way, the three-dimensional image is binarized in response to brightness at each position. Referring to an OCT image showing the original image data visually, in three-dimensional space covered in an imaging range, a region of high reflected light intensity, namely, a region with high density of materials to reflect light is expressed in high brightness. By contrast, a region of low density of materials and thus of low reflected light intensity is expressed in low brightness. Binarizing the three-dimensional image allows distinction between a region of density of materials greater than a certain value and other regions.

As described above, a three-dimensional image of an embryo may include structures such as a pellucid zone, a trophectoderm, and a fragment in addition to blastomeres formed by cleavage. These structures are required to be identified for assessment of the embryo in detail. For this purpose, a boundary is first defined between structures in the three-dimensional image. For definition of such a boundary, an image processing algorithm for realizing region segmentation in three-dimensional space such as the publicly-known watershed algorithm may be used, for example. According to the watershed algorithm, a boundary between a projection and a recess in a three-dimensional image resulting from binarization is identified as a boundary between regions.

In a three-dimensional image of an embryo obtained by OCT imaging, however, a result of segmentation by the watershed algorithm does not agree with an actual embryo configuration in many cases. On the basis of knowledge of the inventors of the present application, this is considered to be caused by the unclearness of a boundary between blastomere cells having relatively large configurations, by structures of smaller configurations distributed around the blastomeres such as a pellucid zone, a trophectoderm and a fragment, or by the influence of image noise, for example. In this regard, before implementation of region segmentation by the watershed algorithm, a process is performed for separating a tiny structure from a larger structure in a three-dimensional image. More specifically, a process based on the following principles is performed.

In this example described herein, a processing target is the embryo E2 shown in FIG. 4B. As shown in FIG. 4B, an image of the embryo E2 includes a plurality of cells C formed by cleavage, fragments F distributed around the cells C, and a pellucid zone Z surrounding the cells C and the fragments F.

In a binarized three-dimensional image, a spatial region occupied by a structure will hereinafter be called a "structure internal space." Further, a surface of the structure in the three-dimensional image, namely, a curved surface as a boundary between the structure internal space and space around the structure internal space will be called a "structure surface." To facilitate understanding, in the following description of processing, a two-dimensional image generated by cutting the three-dimensional image along one cross section is used. However, image processing is actually performed on a three-dimensional image represented by voxel data.

Figure 6A:
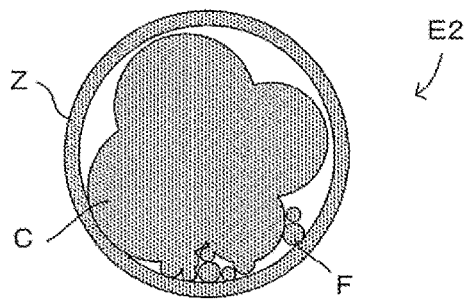
FIG. 6A is a first drawing showing the principles of the process of separating a large structure and a small structure from each other.
Figure 6B:
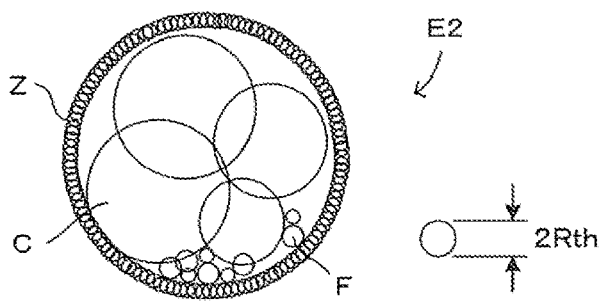
FIG. 6B is a second drawing showing the principles of the process of separating a large structure and a small structure from each other.
Figure 6C:
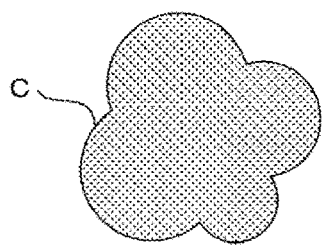
FIG. 6C is a third drawing showing the principles of the process of separating a large structure and a small structure from each other.

FIGS. 6A through 6D show the principles of the process of separating a large structure and a small structure from each other. FIG. 6A shows a two-dimensional image corresponding to the binarized image of the embryo E2 shown in FIG. 4B. As shown in FIG. 6B, under the basic principles of this process, a binarized image is modeled as an aggregate of inscribed spheres (in the two-dimensional image, inscribed circles). Then, distinction is made between a region expressed as an inscribed sphere of a larger radius than an appropriate threshold (a "first threshold" of the present invention) (this region will hereinafter be called a "first region") and a region expressed as an inscribed sphere of a smaller radius than the threshold (this region will hereinafter be called a "second region"). In a case of an inscribed sphere of a radius equal to the threshold, determination is made freely as to whether this sphere is to be included in the first region or in the second region. According to such a model, relatively large structures such as the cell C and an agglutination of the cells C are expressed as an aggregate of inscribed spheres of relatively large radii. On the other hand, small structures such as the pellucid zone Z and the fragment F are expressed as an aggregate of inscribed spheres of smaller radii. Thus, foregoing purpose is achieved by making distinction between structures according to the magnitudes of radii of inscribed spheres. For example, erasing structures expressed as inscribed spheres of radii equal to or less than a threshold Rth shown in FIG. 6B makes it possible to extract only a region corresponding to an aggregate of cells having large configurations, as shown in FIG. 6C.

In principle, a structure can be modeled by making the following calculation. Of points in structure internal space, a point is found at which an inscribed sphere inscribed in a structure surface is given a maximum radius centered on this point, namely, at which a distance to a structure surface is maximum. This inscribed sphere can be identified using the position of the center and the magnitude of the radius. Such a point is not always limited to one point. Next, of points in the structure internal space not included in the inscribed sphere already identified, a point is found at which an inscribed sphere inscribed in the structure surface is given a maximum radius centered on this point. Such a process is repeated until all the points in the structure internal space are included in at least one inscribed sphere, thereby expressing a structure as an aggregate of inscribed spheres.

It takes long time to converge the foregoing calculation. For example, the local thickness calculation algorithm has been suggested as a calculation method available for use for acquiring comparable results in shorter time ("Computing Local Thickness of 3D Structures with ImageJ," Robert P. Dougherty and Karl-Heinz Kunzelmann, Microscopy &

Microanalysis 2007 Meeting, August 5-9, Broward County Convention Center, Ft. Lauderdale, Fla., for example). This method is also applicable to this embodiment. According to this calculation, of spheres including each point in an object in an image and inscribed in a structure surface, a sphere of a maximum radius is searched for. Then, this point is given a higher score as the radius of the inscribed sphere increases. A result of the calculation is output in a way of display such that a point of a higher score is given a higher gradation value (brightness value).

As described above, according to the local thickness calculation, an object in a three-dimensional image is expressed by a gradation value responsive to the magnitude of the radius of a sphere inscribed in this object. Thus, a relatively large object is converted in gradation to a relatively high gradation value (brightness value), and a relatively small object is converted in gradation to a relatively low gradation value (brightness value). Using these gradation values (brightness values) as index values for making distinction between objects makes it possible to distinguish between a relatively large object such as a cell and a tiny objet such as a fragment. In addition to this, a boundary between cells becomes clear to allow proper segmentation between regions.

Figure 6D:
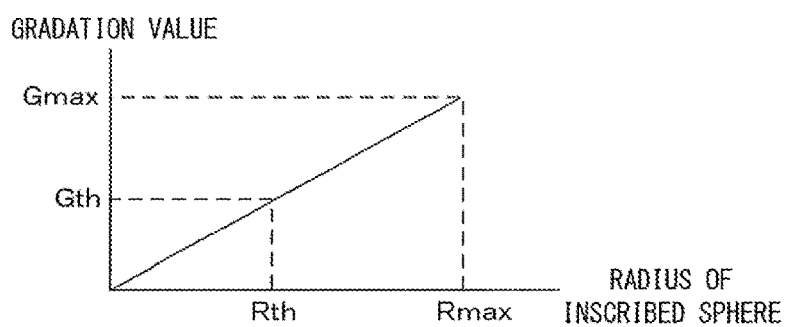
FIG. 6D is a fourth drawing showing the principles of the process of separating a large structure and a small structure from each other.

As shown in FIG. 6D, for example, a maximum gradation value Gmax is assigned to a point at which an inscribed sphere has a radius of a maximum Rmax, and a gradation value is assigned to each point in the structure internal space in such a manner that a gradation value becomes lower with reduction in the radius of an inscribed sphere. It is assumed that a threshold Gth corresponding to a gradation value determined with the radius of an inscribed sphere being the threshold Rth is set for a gradation value at each point obtained by the local thickness calculation. In this case, a point given a gradation value greater than the threshold Gth can be considered to exist inside the first region included in a relatively large configuration. By contrast, a point given a gradation value less than the threshold Gth can be considered to exist inside the second region included in a relatively small configuration.

As described above, the cell C formed by cleavage and an agglutination of the cells C, or a blastomere and an aggregate of blastomeres have relatively large configurations. Namely, a region classified in the first region in the foregoing processing can be judged to be a region occupied by a cell, a blastomere, or an aggregate of cells or blastomeres. By contrast, a region classified in the second region can be judged to be a region occupied by a structure different from a cell agglutination, namely, a region occupied by the pellucid zone Z or the fragment F.

The pellucid zone Z is a continuous thin layer covering the surface of the embryo. The fragment F is a small mass isolated from a blastomere or an aggregate of blastomeres. For this reason, of regions classified in the second region, a region having a sphericity greater than an appropriate threshold (a "second threshold" of the present invention) can be judged to be the fragment F, for example. Of regions of small sphericities, a region having a volume equal to or greater than a predetermined value can be judged to be the pellucid zone Z, and the other regions can be judged to be pseudo structures due to image noise. Separating a tiny structure from a blastomere or an aggregate of blastomeres in this way makes it possible to determine quantitative information such as a shape or a size from a corresponding three-dimensional image.

In this way, information useful for assessment of these structures become available to a user. For example, information such as the number and sizes of fragments is information for assisting in classification of embryos effectively under Veeck classification.

Figure 7A:
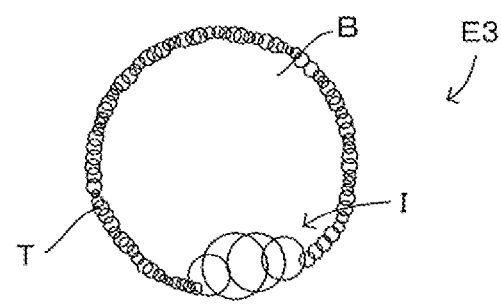
FIG. 7A is a first drawing showing an example of application to a blastocyst.
Figure 7B:
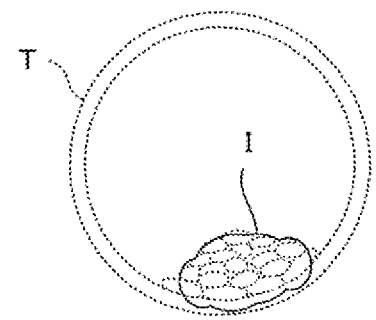
FIG. 7B is a second drawing showing an example of application to a blastocyst.

FIGS. 7A and 7B show an example of application to a blastocyst. As is also shown in FIG. 4C, the blastocyst E3 includes the inner cell mass I as a relatively large structure existing inside the trophectoderm T as a thin layer of cells. For this reason, as shown in FIG. 7A, while the trophectoderm T is expressed as an aggregate of inscribed spheres of small radii, the inner cell mass I is expressed as an aggregate of larger inscribed spheres. As a result, as indicated by a solid line in FIG. 7B, a region corresponding to the inner cell mass I can be extracted by cutting out a region expressed by the inscribed spheres of large radii from a binarized image modeled in this way. Further, a region corresponding to the trophectoderm T can be extracted by cutting out a region expressed by the inscribed spheres of small radii.

The image processing method of this embodiment will be described continuously by referring back to FIG. 5. Calculation based on the foregoing principles, which is the local thickness calculation, for example, is performed on the binarized image (step S104). By doing so, objects in the binarized image are classified into a region corresponding to an aggregate of blastomeres (first region) and the other region (second region). This allows these regions to be expressed individually using quantitative information, as described above. Of these regions, the first region becomes a processing target for the purpose of assessing blastomeres individually included in the cell aggregate.

More specifically, after the second region in which an inscribed sphere has a radius of less than the threshold Rth is removed from the binarized image (step S105), only the first region corresponding to the blastomere aggregate remains. This first region is subjected to region segmentation process by the watershed algorithm (step S106). As a result, individual cells forming the blastomere aggregate are separated from each other. As the fragment F to cause error is removed, use of the watershed algorithm allows a boundary between the individual cells to be defined with high accuracy. Algorithms already used practically as libraries of general-purpose image processing software are available for use both as the local thickness calculation algorithm and the watershed algorithm.

By identifying a region occupied by each cell in the three-dimensional space in the foregoing way, it becomes possible to easily determine the size of each cell in terms of volume or surface area, for example (step S107). For example, variations in volume of the cells forming the blastomere aggregate are available for use as indexes for judging whether the condition of an embryo is good or bad under Veeck classification.

To assess each cell in more detail, an index value responsive to the shape of the cell can be introduced. Each cell is considered to have a practically spherical shape in an independent condition. In a blastomere aggregate as a group of a plurality of cells, however, deformation occurs, particularly in a part contacting another cell. At a site of embryo culture, there is a finding that a cell preferably has a smooth surface and such a feature relating to a shape is desired to be expressed quantitatively.

In this regard, according to this embodiment, each region identified as one cell is approximated to an ellipsoid (step S108). Then, a degree of divergence between the surface of each cell and the surface of the approximate ellipsoid is expressed quantitatively, thereby responding to the foregoing desire. The details thereof will be explained next. This explanation will be given using two cells contacting each other. However, this explanation will also apply to a blastomere aggregate with a larger number of cells contacting each other.

Figure 8A:
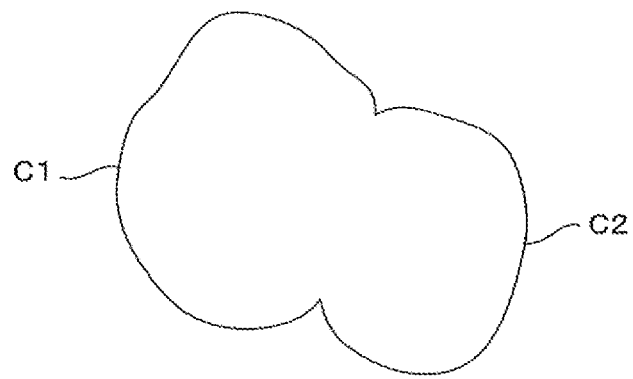
FIG. 8A is a first drawing schematically showing separation between individual cells using the region segmentation.
Figure 8B:
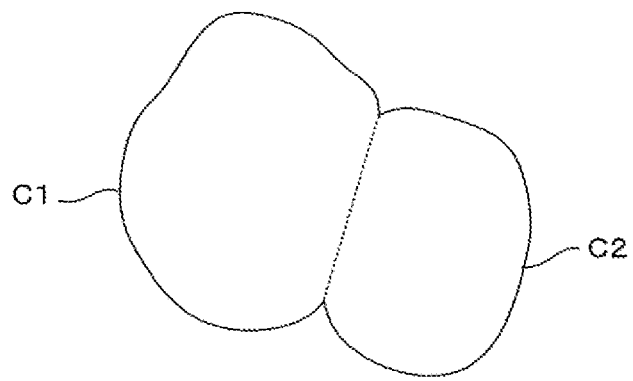
FIG. 8B is a second drawing schematically showing separation between individual cells using the region segmentation.
Figure 8C:
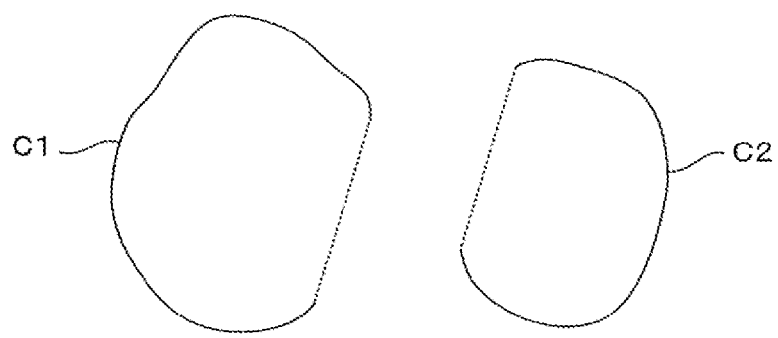
FIG. 8C is a third drawing schematically showing separation between individual cells using the region segmentation.

FIGS. 8A through 8C schematically show separation between individual cells using the region segmentation. FIGS. 9A through 9D schematically show approximation of a cell to an ellipsoid. As shown in FIG. 8A, in the binarized image in a state before the region segmentation, two cells C1 and C2 are expressed as an integrated object. As a result of implementation of the region segmentation process by the watershed algorithm, a boundary between the two cells C1 and C2 is defined, as shown in FIGS. 8B and 8C. In this way, these regions are separated as independent objects in the three-dimensional space. In FIG. 8C, solid lines show the contours of the surfaces of cells exposed without contacting another surface (hereinafter called "exposed surfaces"), and dotted lines show boundaries between cells defined by the implementation of the region segmentation process.

The cell resulting from the foregoing segmentation is considered to form a sphere or an ellipsoid as viewed in its entirety. However, the cell may be deformed largely at a part contacting another cell. Thus, information only about an exposed surface as a part of the surface of the region resulting from the segmentation and not contacting another cell is used for the approximation to an ellipsoid. This achieves reduction in error to be caused by the deformation of the cell.

More specifically, the exposed surface is extracted first. Namely, a binarized image of a cell region resulting from the segmentation is subjected to dilation process by one pixel to form an image corresponding to the logical product of each pixel between this region and a peripheral region of the blastomere aggregate in the binarized image before the segmentation. As a result, an image of the exposed surface having a thickness corresponding to one pixel is obtained. A boundary surface formed by the segmentation is included inside the source blastomere aggregate, so that it does appear in a result of the logical product.

An approximate ellipsoid is obtained from the resultant shape of the exposed surface. More specifically, by using the space coordinates (x, y, z) of each point included in the exposed surface and the following formula that is a general expression for an ellipsoid:

$$Ax^2+By^2+Cz^2+Dxy+Exz+Fyz+Gx+Hy+Iz+J=0,$$

each of the constants A to J is determined by the least-squares method, for example. This makes it possible to identify an ellipsoid as an approximation of the foregoing region. As indicated by dashes in FIG. 9A, an approximate ellipsoid Ea1 corresponding to the cell C1 is an approximation of the shape of the exposed surface of the cell C1 indicated by a solid line, and does not always agree with a boundary defined by the region segmentation indicated by a dotted line. Namely, the approximate ellipsoid Ea1 is free from the influence of the deformation of the cell C1 to be caused by contact with another cell. This also applies to an approximate ellipsoid Ea2 corresponding to the cell C2.

As described above, representing each cell approximately as an ellipsoid allows the shape of the cell to be expressed quantitatively using a parameter indicating this shape. Examples of the parameter to be used include the lengths of a major axis and a minor axis, a volume, oblateness, and a direction of the major axis. This allows assessment of the shape of each cell, comparison in shape between a plurality of cells, and others to be made easily and quantitatively.

At the exposed surface of the cell C1, complete agreement is also absent between a non-smooth surface and the surface of the approximate ellipsoid Ea1. In this regard, if a cell is in a favorable condition and has a smooth surface, a degree of divergence between the surface of an approximate ellipsoid and an exposed surface is considered to be small. Namely, a numerical value indicating a degree of divergence between the exposed surface of the cell and the surface of the approximate ellipsoid can be an index value indicating the condition of the cell quantitatively.

Figure 9A:
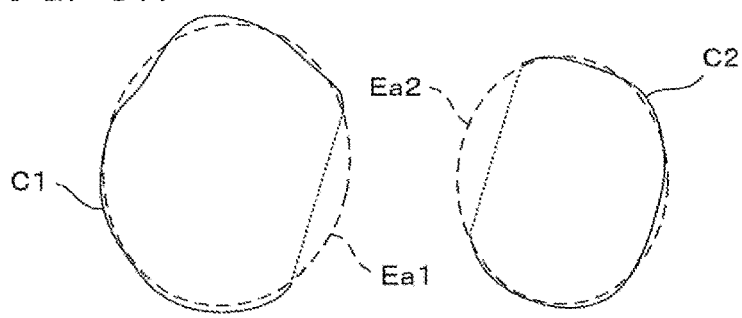
FIG. 9A is a first drawing schematically showing approximation of a cell to an ellipsoid.
Figure 9B:
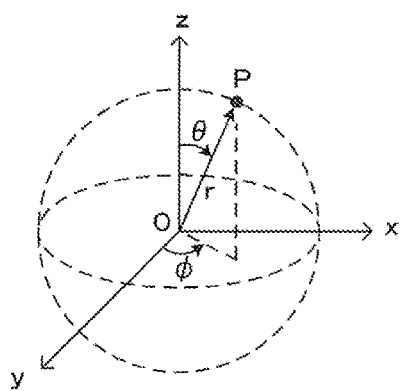
FIG. 9B is a second drawing schematically showing approximation of a cell to an ellipsoid.

To derive such an index value, the coordinates of each point on a cell surface is expressed using polar coordinates. In the original image data (voxel data) acquired by beam scanning on an imaging subject in the X and Y direction, each position in the three-dimensional space is expressed in the xyz coordinate system. However, the schematic shape of a cell can be expressed as an ellipsoid. Thus, to express the shape of the cell more directly, it is preferable to represent each position using spherical coordinates with an origin set at the center of the cell. Then, as shown in FIG. 9B, coordinate conversion is performed from the xyz orthogonal coordinate system to an rθφ spherical coordinate system using a moving radius r and two deflection angles θ and φ as coordinate variables.

As is well known, there is a relationship expressed by the following formulas between the coordinates (x, y, z) of a point P in the orthogonal coordinate system and the coordinates (r, θ, φ) of the point P in the spherical coordinate system if an origin O is common between the coordinate systems:

$$x=r\sin\theta\cos\varphi,$$

$$y=r\sin\theta\sin\varphi,\text{ and}$$

$$z=r\cos\theta.$$

These coordinates are mutually convertible.

More specifically, the centroid of an approximate ellipsoid determined previously is defined as the origin O of the spherical coordinate system. The origin O is not required to agree with the origin of the xyz orthogonal coordinate system in the original image data. Then, coordinate conversion is performed from the orthogonal coordinates to the spherical coordinates through appropriate converting process (step S109). As a result of the coordinate conversion performed in this way, each position in the three-dimensional space identified in the xyz orthogonal coordinate system is expressed in the rθφ spherical coordinate system. The centroid of the ellipsoid can be the midpoint of a line segment representing the major axis or the minor axis of the ellipsoid, for example.

Figure 9C:
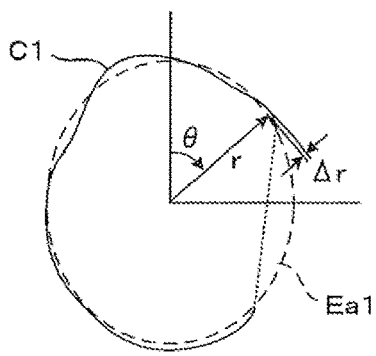
FIG. 9C is a third drawing schematically showing approximation of a cell to an ellipsoid.
Figure 9D:
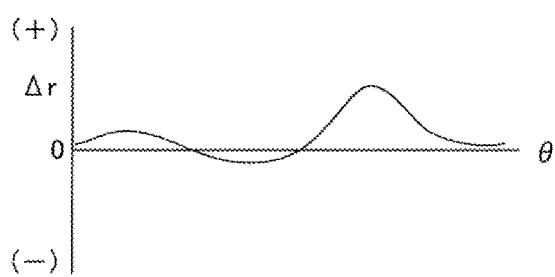
FIG. 9D is a fourth drawing schematically showing approximation of a cell to an ellipsoid.

As a result of the coordinate conversion performed in this way, each point on the exposed surface of the cell C1 (C2) and each point on the surface of the approximate ellipsoid Ea1 (Ea2) are expressed using polar coordinates. As shown in FIGS. 9C and 9D, a distance Δr in one direction of the moving radius r between the exposed surface of the cell C1 (C2) and the surface of the approximate ellipsoid Ea1 (Ea2) is determined, and then the determined distance Δr can be used as a value indicating a degree of divergence in this direction between the cell and the ellipsoid. Namely, it can be said that divergence between the surface of the cell and the surface of the ellipsoid becomes smaller with reduction in the distance Δr, and the divergence becomes more noticeable with increase in the distance Δr.

A degree of divergence of the cell C1 as a whole from the approximate ellipsoid Ea1 can be expressed, for example, by determining the distance Δr in each moving radius direction through the entire exposed surface in the same way as that described above, and by using an index value determined from at least one of a maximum of the distance Δr, a difference between the maximum and a minimum, and a value of integral of the absolute of the difference, etc. (step S110). By expressing a position using the spherical coordinates, it becomes possible to make such calculation in a simple way for quantitatively comparing a cell and its approximate ellipsoid. These index values are considered to be indexes to a degree of distortion of the cell. With reduction in these index values, the cell is given a smoother surface with less distortion and thus the cell is estimated to be a favorable cell.

As described above, each structure can be assessed in terms of a shape on the basis of a binarized image resulting from binarization of a three-dimensional image obtained by OCT imaging. In the meantime, to assess a degree of fullness or uniformity inside each structure, information about the contrast of a three-dimensional object resulting from a difference in density between structures is required.

Here, a binarized image is prepared as a mask in which each cell and other structures are classified into corresponding regions as described above, and a three-dimensional image including contrast expressed in the original image data is masked with this image. This allows a three-dimensional object in the original image to be cut out individually on the basis of each region. Namely, an image corresponding to the logical product of each pixel between the original image and the binarized image resulting from the region segmentation is generated (step S111), thereby obtaining an image showing the original image after the region segmentation. A comparable result is also achieved by segmenting three-dimensional objects in the original image with a boundary defined by the foregoing region segmentation.

As a result, contrast in each region resulting from the segmentation is expressed by a pixel value (brightness value) of each pixel in this region. This information is available for use for assessment of the internal configuration of this region individually. As an example, average intensity in a region resulting from the segmentation is an index value indicating average density of a material in this region and is information helpful for distinguishing between a cell including a nucleus and a fragment not including a nucleus, for example. In another example, an intensity histogram is generated about each region resulting from the segmentation on the basis of a brightness value inside the region (step S112). This makes it possible to acquire information useful for estimating an internal configuration. Generating an intensity histogram covering one region in its entirety allows representation of the property of this region in its entirety. Generating an intensity histogram about a part of one region allows representation of a configuration inside the region in further detail.

Figure 10A:
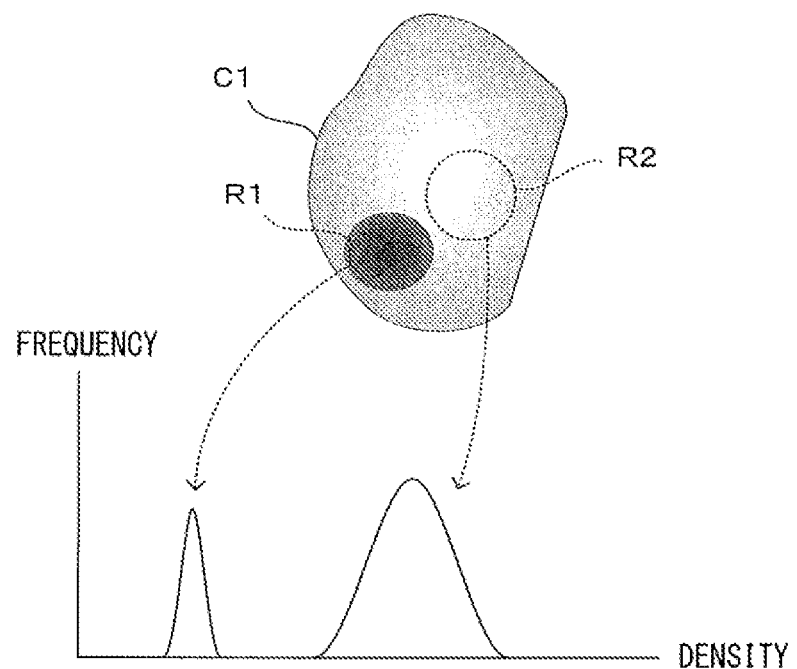
FIG. 10A is a first drawing showing examples of intensity histograms.
Figure 10B:
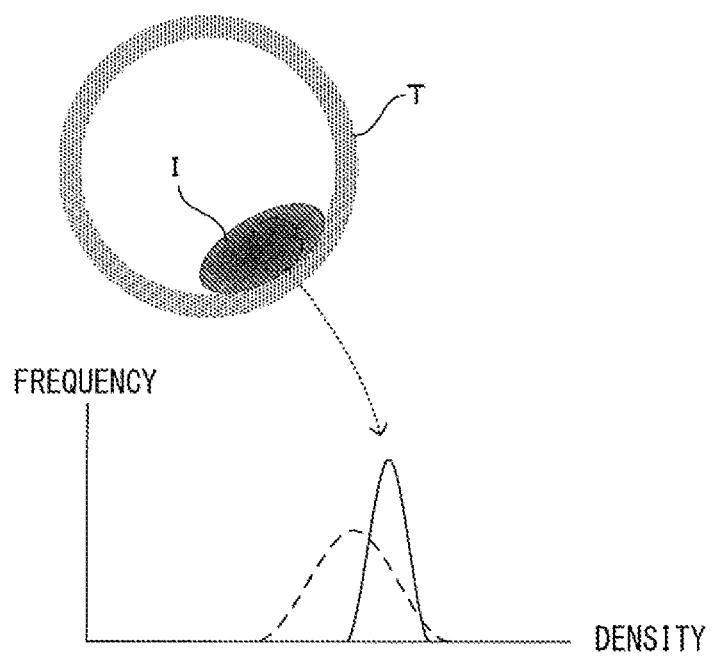
FIG. 10B is a second drawing showing examples of intensity histograms.

FIGS. 10A and 10B show examples of intensity histograms. FIG. 10A shows intensity histograms about two regions R1 and R2 inside the cell C1 defined by the region segmentation. According to the intensity histogram about the region R1, a narrow peak is observed in a relatively low intensity range. This region can be estimated to be a region of low substance density such as a cavity, for example. On the other hand, regarding the region R2, a wide peak is observed in a relatively high intensity range, which shows that materials are included at high density and locally in this region. Such tendency is observed, for example in a region where organelles are concentrated in a cell or in a region in the presence of active motion for cell division.

An intensity histogram is also considered to differ largely between a nucleus region and other regions in a cell. Obtaining an intensity histogram in this way allows provision of information to a user to become a clue to the internal configuration of a cell such as the position, height, and width of a peak, for example.

The foregoing technique of obtaining an intensity histogram is also useful for assessment of a blastocyst. As shown in FIG. 10B, in the blastocyst, the inner cell mass I is formed inside the trophectoderm T. In an embryo in a good condition, the inner cell mass I is formed of a large number of dense cells. On the other hand, an inner cell mass in an embryo not in such a condition may be in a case with a small number of cells or in a sparse condition of low density. For this reason, when an intensity histogram is obtained about the inner cell mass I identified by the region segmentation, the extent of a peak is small in an embryo in a good condition as shown by a solid line in the lower graph of FIG. 10B. By contrast, in an embryo not in a good condition, the extent of a peak is larger as shown by dashes. In this way, information about the inner cell mass I as indexes such as the position, height, and the width of a peak are also available for use for assessment of an embryo. For example, by applying such index values to Gardner classification, it becomes possible to make classification quantitatively that has conventionally depended on a subjective judgment.

As described above, in this embodiment, a three-dimensional image obtained by OCT imaging of an embryo is available for use for identifying a region individually corresponding to each of various types of structures such as a cell and a fragment. An index value indicating a feature of each identified region quantitatively is calculated for each identified region, thereby obtaining information useful for assessment of each region as an objective numerical value. In this embodiment, providing such an index value to a user in a way such as displaying the same on the display section 352, for example, allows assistance in assessment of an embryo by the user effectively.

Structures in a three-dimensional image may include various types of structures such as blastomeres, cells, and fragments. By setting appropriate thresholds in advance for index values determined in the foregoing way, it becomes possible to carry out the present invention as an image judging method of judging the type of a structure automatically.

The invention is not limited to the foregoing embodiment but various changes other than those described above can be made without departing from the gist of the invention. For example, the image processing apparatus 1 of the foregoing embodiment has the function of OCT imaging the sample Sp, and the function of generating an output image from imaging data and outputting the generated image. However, the image processing method of the present invention can also be implemented by a computer device not having its own imaging function but to acquire imaging data obtained by imaging by a different apparatus having an imaging function. To achieve this, the present invention may be carried out as a software program for causing the computer device to perform steps from step S102 to S112 of all the process steps in FIG. 5.

Such a program can be distributed in a form of downloading the program through a telecommunication line such as the Internet, for example. Alternatively, the program may be distributed by distributing a computer-readable storage medium storing this program. In another case, the present invention can be carried out using an existing OCT image processing apparatus by causing this image processing apparatus to read the program through an interface.

As another example, for the purpose of assessing a cell individually forming a blastomere aggregate, the forgoing embodiment includes the process performed for erasing the second region corresponding to a fragment, which is a region of those classified by the local thickness calculation. However, for the purpose of observing a fragment in detail, for example, the first region may be erased while the second region remains unerased. Alternatively, images for expressing the first region and the second region individually may be generated.

As another example, the image processing in the foregoing embodiment (FIG. 5) includes the process for the region segmentation of a three-dimensional image of an embryo (steps S104 to S106), the calculation of the sizes of regions resulting from the segmentation (step S107), the process of approximating each cell to an ellipsoid (step S108), the process of expressing the surface of a cell using polar coordinates (step S109), the process of determining a degree of divergence between the cell and the approximate ellipsoid (step S110), and the process of determining an intensity distribution within a region (steps S111 to S112) performed in this order. However, performing all these processes is not an absolute necessity but a required process responsive to a purpose may be selected and performed appropriately. Also, the order of performing the processes is not limited to the foregoing order.

Furthermore, the foregoing embodiment is to present various types of quantitative information useful for assessment by a user from a three-dimensional image obtained by OCT imaging. A way in which these pieces of information are used by the user is not limited to the foregoing example but can be determined freely.

As seen from the specific embodiment illustrated and described above, in the image processing method according to the present invention, a gradation value given to each point in a three-dimensional image by the local thickness calculation can be used as an index value. According to the local thickness calculation algorithm made public in a form of being available to general users, the size of an object is expressed by a gradation value. Such a gradation value is preferably applicable to an index value to be used in the foregoing processing.

As another example, the region segmentation step may be configured in such a manner as to define boundaries between a plurality of regions, and to segment a three-dimensional image expressed by original image data into pieces at the defined boundaries. Segmenting objects in the three-dimensional image at these boundaries makes it possible to separate individual cells as blastomeres and other structures from each other and assess the separated structures.

As another example, a region resulting from the segmentation may be configured in such a manner that an exposed surface, which is a part of the surface of the region and not contacting another region, is approximated to an ellipsoid. While a cell has an indefinite shape, it is practically ellipsoidal. Thus, approximating the cell to an ellipsoid allows the shape of the cell to be expressed as a specific numerical value. In this case, a part of the cell contacting another cell is deformed at the surface. Thus, approximating the exposed surface less prone to such deformation to an ellipsoid allows reduction in error due to the surface deformation.

In this case, an index value indicating a degree of divergence between the surface of an approximate ellipsoid obtained by the ellipsoid approximation and the exposed surface may further be calculated, for example. The approximate ellipsoid can be said to be a shape indicating an ideal shape of a cell, so that a level of divergence to occur becomes an indication of a distortion level of the cell or a non-smoothness level of the surface of the cell. An index value indicating such a feature about a shape quantitatively becomes useful for assessment by a user.

As another example, the coordinates of each position on an exposed surface and those of each position on the surface of an approximate ellipsoid may be expressed using polar coordinates with an origin set at the centroid of the approximate ellipsoid, and an index value may be determined on the basis of a distance between a point on the exposed surface and a point on the surface of the approximate ellipsoid along the same moving radius. A distance between a cell and the approximate ellipsoid viewed from the centroid of the ellipsoid is available for use as information directly indicating a degree of divergence therebetween.

As another example, a histogram about a pixel value of each pixel in a region resulting from the segmentation may be calculated. This configuration allows generation of information showing the internal configuration of a cell quantitatively.

The image processing method according to the present invention can be configured to segment a three-dimensional image of an embryo into a plurality of regions by the foregoing method, and to judge the first region of these regions indicated by an index value greater than the first threshold to be a blastomere aggregate. A normal blastomere in an embryo is considered to have a larger configuration than the other structures. Thus, judging the first region, which is estimated to have a relatively large configuration, to be a blastomere aggregate is strongly rational.

In this case, one region segmented further from the first region may be judged to be one cell. If the first region is considered to be a blastomere formed of a plurality of cells, each region resulting from the further segmentation of the blastomere is reasonably considered to be a region corresponding to one cell.

As another example, of regions classified in the second region indicated by an index value less than the first threshold, a region having a sphericity greater than the second threshold may be judged to be a fragment. While a fragment has a smaller configuration than a cell, it has a certain sphericity. Thus, of regions classified in the second region, a region having a relatively high sphericity can be considered to be a fragment. This makes it possible to distinguish between the fragment and other structures.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

INDUSTRIAL APPLICABILITY

The present invention is applicable to a purpose of assisting in assessment of the condition of a cultured embryo. For example, the present invention is available for use for increasing a success rate of external fertilization or artificial fertilization in fertility treatment.

REFERENCE SIGN LIST

1 image processing apparatus
10 holder 20 imaging unit
21 light source
22 beam splitter
24 reference mirror
26 photo-detector
30 control unit
33 signal processor
34 3D restoration section
352 display section
Sp sample

The invention claimed is:

1. An image processing method comprising:
acquiring original image data corresponding to a three-dimensional image of a cultured embryo obtained by optical coherence tomography imaging of the embryo; and
executing a region segmentation of the three-dimensional image into a plurality of regions on the basis of the original image data, wherein in the region segmentation,
a local thickness calculation is performed on the three-dimensional image to determine an index value indicating a size of an object included in the three-dimensional image,
the three-dimensional image is segmented into a region indicated by the index value greater than a predetermined first threshold and a region indicated by the index value less than the first threshold, and
each of the regions resulting from the segmentation is further segmented by a watershed algorithm.

2. The image processing method according to claim 1, wherein a gradation value given to each point in the three-dimensional image by the local thickness calculation is used as the index value.

3. The image processing method according to claim 1, wherein the region segmentation is configured in such a manner as to define boundaries between a plurality of regions, and to segment the three-dimensional image expressed by original image data into pieces at the boundaries.

4. The image processing method according to claim 1, wherein a region resulting from the region segmentation is configured in such a manner that an exposed surface, which is a part of a surface of the region and not contacting another region, is approximated to an ellipsoid.

5. The image processing method according to claim 4, wherein an index value indicating a degree of divergence between a surface of an approximate ellipsoid obtained by an ellipsoid approximation and the exposed surface is calculated.

6. The image processing method according to claim 5, wherein coordinates of each position on the exposed surface and coordinates of each position on the surface of the approximate ellipsoid are expressed using polar coordinates with an origin set at a centroid of the approximate ellipsoid, and the index value is determined based on a distance between a point on the exposed surface and a point on the surface of the approximate ellipsoid along a same moving radius.

7. The image processing method according to claim 1, wherein a histogram about a pixel value of each pixel in each region resulting from the region segmentation segmented by the local thickness calculation and the watershed algorithm is calculated.

8. The image processing method according to claim 1, wherein the three-dimensional image of the embryo is segmented into a plurality of regions by the region segmentation, and out of these regions, a first region having the index value greater than the first threshold is judged to be a blastomere aggregate.

9. The image processing method according to claim 8, wherein one region segmented further from the first region is judged to be one cell.

10. The image processing method according to claim 8, wherein out of regions segmented from a second region having the index value less than the first threshold, a region having a sphericity greater than a second threshold is judged to be a fragment.

11. A non-transitory computer-readable recording medium having recorded therein a program for performing an image processing including:
acquiring original image data corresponding to a three-dimensional image of a cultured embryo obtained by optical coherence tomography imaging of the embryo; and
executing a region segmentation of the three-dimensional image into a plurality of regions on the basis of the original image data, wherein in the region segmentation,
a local thickness calculation is performed on the three-dimensional image to determine an index value indicating a size of an object included in the three-dimensional image,
the three-dimensional image is segmented into a region indicated by the index value greater than a predetermined first threshold and a region indicated by the index value less than the first threshold, and
each of the regions resulting from the segmentation is further segmented by a watershed algorithm.

* * * * *